United States Patent
Clarke et al.

(10) Patent No.: US 11,911,439 B2
(45) Date of Patent: Feb. 27, 2024

(54) BETA-CASEIN A2 AND PREVENTION OF INFLAMMATION OF THE BOWEL

(71) Applicant: THE A2 MILK COMPANY LIMITED, Auckland (NZ)

(72) Inventors: Andrew John Clarke, Auckland (NZ); Malav Suchin Trivedi, Hollywood, FL (US)

(73) Assignee: THE A2 MILK COMPANY LIMITED, Auckland (NZ)

( * ) Notice: Subject to any disclaimer, the term of this patent is extended or adjusted under 35 U.S.C. 154(b) by 0 days.

(21) Appl. No.: 16/784,911

(22) Filed: Feb. 7, 2020

(65) Prior Publication Data

US 2020/0179485 A1 Jun. 11, 2020

Related U.S. Application Data

(63) Continuation of application No. 14/894,711, filed as application No. PCT/NZ2014/000102 on May 30, 2014, now abandoned.

(60) Provisional application No. 61/829,764, filed on May 31, 2013.

(51) Int. Cl.
| | |
|---|---|
| *A61K 38/17* | (2006.01) |
| *A61K 35/20* | (2006.01) |
| *A23K 20/147* | (2016.01) |

(52) U.S. Cl.
CPC ........ *A61K 38/1709* (2013.01); *A23K 20/147* (2016.05); *A61K 35/20* (2013.01)

(58) Field of Classification Search
None
See application file for complete search history.

(56) References Cited

U.S. PATENT DOCUMENTS

| | | |
|---|---|---|
| 2006/0280802 A1 | 12/2006 | Campbell et al. |
| 2012/0070469 A1 | 3/2012 | Barenholz et al. |

FOREIGN PATENT DOCUMENTS

| | | |
|---|---|---|
| WO | 96/14577 A1 | 5/1996 |
| WO | 96/36239 A1 | 11/1996 |
| WO | 01/00047 A1 | 1/2001 |
| WO | 02/19832 A1 | 3/2002 |
| WO | 2004/030690 A1 | 4/2004 |
| WO | 2008/041219 A1 | 4/2008 |

OTHER PUBLICATIONS

Milan et al. The American Journal of Clinical Nutrition. vol. 111, Issue 1, Jan. 2020, pp. 149-160. https://www.sciencedirect.com/science/article/pii/S0002916522009820#bib26.*

Vernia et al. Lactose malabsorption, irritable bowel syndrome and self-reported milk intolerance Dig Liver Dis., 33 (2001), pp. 234-239.*

Monsbakken et al. Perceived food intolerance in subjects with irritable bowel syndrome-etiology, prevalence and consequences Eur J Clin Nutr., 60 (2006), pp. 667-672.*

Almazar et al. Comparison of lactase variant MCM6 -13910 C→T testing and self-report of dairy sensitivity in patients with irritable bowel syndrome. J Clin Gastroenterol., 53 (2019), pp. e227-e273.*

Drossman. The functional gastrointestinal disorders and the Rome III process. Gastroenterology., 130 (2006), pp. 1377-1390.*

Casellas et al. Development, validation, and applicability of a symptoms questionnaire for lactose malabsorption screening Dig Dis Sci., 54 (2009), pp. 1059-1065.*

Giribaldi et al. A2 Milk and BCM-7 Peptide as Emerging Parameters of Milk Quality. Front Nutr. Apr. 27, 2022;9:842375. doi: 10.3389/fnut.2022.842375. PMID: 35571904; PMCID: PMC9094626.*

Barnett et al., Changes in colon gene expression associated with increased colon inflammation in interleukin-10 gene-deficient mice inoculated with Enterococcus species, BMC Immunal., 11:39 (2010).

Cassar, A2 milk—fleckvieh reveals another secret!, Flekvieh world, available online at <http://www.fleckvieh.de/FleckviehweltAA/orld/FVW_2010/world-22-24.pdf>, (2011).

Charlin et al., Treatment of acute secretory diarrhea with casein: and effect of beta-casomorphins? Rev. Med. Chil., 120(6):666-9 (1992).

Chatterton et al., Anti-inflammatory mechanisms of bioactive milk proteins in the intestine of newborns, Int. J. Biochem. Cell Biol., 45(8):1730-1747 (2013).

Chin-Dusting et al., British Journal of Nutrition, "Effect of dietary supplementation with 13-casein A1 or A2 on markers of disease development in individuals at high risk of cardiovascular disease", 95:136-144 (2006).

Clemens et al., Nestle Nutr. Inst. Workshop Ser Pediatr Program, "Milk A1 and A2 Peptides and Diabetes", vol. 67:187-195 (2011).

Crowley et al., Does milk cause constipation? A crossover dietary trial, Nutrients, 5:253-66 (2013).

Deth et al., Nutrition Journal, "Clinical evaluation of glutathione concentrations after consumption of milk containing different subtypes of B-casein: results from a randomized, cross-over clinical trial", 15:82 (2016).

Dommels et al., Characterization of intestinal inflammation and identification of related gene expression changes in mdr1a(-/-) mice, Genes Nutr., 2(2):209-23 (2007).

Elitsur et al., Beta-casomorphin (BCM) and human colonic lamina propria lymphocyte proliferation, Clin. Exp. Immunol., 85(3):493-7 (1991).

European food safety assocation, Review of the potential health impact of (3-casomorphins and related peptides, Report of the DATEX working group on (3-casomorphins. (Question No. EFSA-Q-2008-379), EFSA scientific report, 231:1-107 (2009).

Fuller, Science or Snake Oil: is A2 milk better for you than regular cow's milk?, The Conversation, (2016). http://theconversation.com/science-or-snake-oil-is-a2-milk-better-for-you-than-regular-cows-milk-62486.

Grisham et al., Assessment of leukocyte involvement during ischemia and reperfusion of intestine, Methods Enzymol., 186:729-42 (1990).

(Continued)

*Primary Examiner* — Maury A Audet
(74) *Attorney, Agent, or Firm* — MARSHALL, GERSTEIN & BORUN LLP

(57) ABSTRACT

The use of a composition for preventing or reducing the risk of inflammation of the bowel in an animal, wherein the composition contains beta-casein and wherein the beta-casein comprises at least 50% by weight beta-casein A2.

4 Claims, 7 Drawing Sheets

(56) References Cited

OTHER PUBLICATIONS

Gunn et al., A comparative trial of casein or whey-predominant formulae in healthy infants, NZ Med. J., 99(813):843-6 (1986).

Haq et al., Comparative evaluation of cow (3-casein variants (A1/A2) consumption on Th2-mediated inflammatory response in mouse gut, European journal of nutrition, 53(4):1039-1049 (2014).

Hodgson et al., Soluble oligomers of amyloid-(Beta) cause changes in redox state, DNA methylation, and gene transcription by inhibiting EAAT3 mediated cysteine uptake. Hodason N1, J. Alzh. Dis., 36(1):197-209 (2013).

Kaminski et al., Polymorphism of bovine beta-casein and its potential effect on human health, J. Aool. Gen., 48:189-98 (2007).

Knoch et al., Genome-wide analysis of dietary eicosapentaenoic acid- and oleic acid-induced modulation of colon inflammation in interleukin-10 gene-deficient mice, J. Nutrigenet. Nutriaenomics, 2(1):9-28 (2009).

Krawisz et al., Quantitative assay for acute intestinal inflammation based on myeloperoxidase activity. Assessment of inflammation in rat and hamster models, Gastroenterology, 87(6):1344-50 (1984).

Lewis et al., Stool form scale as a useful guide to intestinal transit time, Scand. J. Gastroenterol., 32(9):920-4 (1997).

Mihatsch et al., Hydrolysis of casein accelerates gastrointestinal transit via reduction of opioid receptor aaonists released from casein in rats, Biol. Neonate, 87(3):160-3 (2005).

Smith et al., Measurement of protein using bicinchoninic acid, Anal. Biochem., 150(1):76-85 (1985).

Trivedi et al., Morphine Induces Redox-Based Changes in Global DNA Methylation and Retrotransposon Transcription by Inhibition of Excitatory Amino Acid Transporter Type 3-Mediated Cystine Update, Mal. Pharm., 85(5):747-57 (2014).

Truswell, European Journal of Clinical Nutrition, "The A2 Milk case: a critical review", 59:623-631 (2005).

Uhler et al., Serum amyloid A, the major vertebrate acute-phase reactant, Fur. 3. Biochem., 265(2):501-23 (1999).

Zhang et al., The protective effects of beta-casomorphin-7 against glucose -induced renal oxidative stress in vivo and vitro, PloS One, 8(5):e63472 (2013).

Zoghbi et al., 13-Casomorphin-7 regulates the secretion and expression of gastrointestinal mucins through a mu-opioid pathway, Am. J. Physiol. Gastrointest. Liver Physiol., 290(6):G1105-13 (2006).

* cited by examiner

BETA-CASEIN A2 AND PREVENTION OF INFLAMMATION OF THE BOWEL

CROSS-REFERENCE TO RELATED APPLICATIONS

This application is a continuation of U.S. patent application Ser. No. 14/894,711, filed Nov. 30, 2015, which in turn is a U.S. national phase pursuant to 35 U.S.C. § 371 of International Patent Application No. PCT/NZ2014/000102 filed May 30, 2014, which in turn claims the benefit of priority under 35 USC 119(e) of U.S. Patent Application No. 61/829,764 filed May 31, 2013.

TECHNICAL FIELD

The invention relates to the use of the milk protein beta-casein A2 for preventing or reducing the risk of inflammation of the bowel. In particular, the invention relates to milk and milk derived food products and the avoidance of consuming milk and milk products that contain high levels of the protein beta-casein A1 which has been shown to cause both immediate and ongoing inflammation of the bowel. The invention relates to the prevention of bowel inflammation, including general bowel irritation as well as inflammatory bowel diseases and irritable bowel syndrome.

BACKGROUND OF THE INVENTION

Inflammation of the bowel can result from a variety of disorders or conditions that are characterised by inflammation of the colon and the small intestine. Such disorders or conditions include inflammatory bowel disease (IBD) and irritable bowel syndrome (IBS). IBD refers generally to clinically defined and persistent conditions, primarily Crohn's disease and ulcerative colitis. IBDs are generally considered to be autoimmune diseases where the body's own immune system attacks elements of the digestive system. IBS is a disorder characterised by abdominal pain or discomfort and altered bowel habit (usually chronic or recurrent diarrhoea, constipation, or both). IBS is said to affect between 25 and 45 million people in the United States alone. Approximately two in every three IBS sufferers are female. IBS affects people of all ages, including children. It is estimated that approximately 10 to 25% of the worldwide population suffer from IBS. The impact of IBS can range from mild inconvenience to severe debilitation. People with moderate to severe IBS struggle with symptoms that often impair their physical, emotional, economic, educational and social well-being.

The exact causes of bowel inflammation are not well understood. However, diet appears to be important, especially in the case of IBS. Milk and milk fats in particular are thought to be one contributing factor. Many bowel inflammation conditions are managed, rather than cured. Often the treatment comprises a combination of dietary care, stress management, and drug therapy.

Milk, mainly bovine milk, consumed in populations throughout the world, is a major source of protein in human diets. Bovine milk typically comprises around 30 grams per litre of protein. Caseins make up the largest component (80%) of that protein. In the past two decades there has been a growing body of evidence implicating casein proteins, especially beta-caseins, in a number of health disorders.

The beta-caseins can be categorised as beta-casein A1 and beta-casein A2. These two proteins are the predominant beta-caseins in the milk consumed in most human populations. Beta-casein A1 differs from beta-casein A2 by a single amino acid. A histidine amino acid is located at position 67 of the 209 amino acid sequence of beta-casein A1, whereas a proline is located at the same position of beta-casein A2. This single amino acid difference is, however, critically important to the enzymatic digestion of beta-caseins in the gut. The presence of histidine at position 67 allows a protein fragment comprising seven amino acids, known as beta-casomorphin-7 (BCM-7), to be produced on enzymatic digestion. Thus, BCM-7 is a digestion product of beta-casein A1. In the case of beta-casein A2, position 67 is occupied by a proline which hinders cleavage of the amino acid bond at that location, Thus, BCM-7 is not a digestion product of beta-casein A2.

Other beta-casein variants, such as beta-casein B and C, also have histidine at position 67, and other variants, such as A3, D and E, have praline at position 67. But these variants are found only in very low levels, or not found at all, in milk from cows of European origin. Thus, in the context of this invention, the term beta-casein A1 refers to any beta-casein having histidine at position 67, and the term beta-casein A2 refers to any beta-casein having proline at position 67.

BCM-7 is an opioid peptide and can potently activate opioid receptors throughout the body. BCM-7 has the ability to cross the gastrointestinal wall and enter circulation enabling it to influence systemic and cellular activities via opioid receptors. The applicant and others have previously determined a link between the consumption of beta-casein A1 in milk and milk products and the incidence of certain health conditions including type I diabetes (WO 1996/014577), coronary heart disease (WO 1996/036239) and neurological disorders (WO 2002/019832).

There has been speculation that BCM-7 can also affect digestive function. It has been reported that opioid receptors play a role in controlling gastrointestinal function, including regulating gastrointestinal motility, mucus production and hormone production. (for example, Mihatsch, W. A, et al., *Biol. Neonate*, 2005, 87(3):160-3). The caseins found in milk are thought to be associated with inhibiting intestinal motility, which can lead to constipation (Gunn T. R. and Stunzer D., *NZ Med. J.*, 1986, 99(813):843-6) and research on casomorphins and synthetic casomorphin derivatives indicates that BCM-7 contributes to this opioid receptor mediated effect (Charlin V. et al., *Rev. Med. Chil.*, 1992, 120(6):666-9). However, while there is some in vitro evidence for a link between casomorphins and transit time in the intestines, it is apparent that the effect cannot necessarily be extrapolated to an in vivo effect in humans. For example, at least one study failed to demonstrate a relationship between beta-casein A1 or beta-casein A2 consumption and constipation (Crowley, E. T., *Nutrients*, 2013, 5, 253-266). BCM-7 has been shown to stimulate the production of mucus via mu-opiate receptor mediated pathways (Zoghbi, S., *Am. J. Physiol. Gastrointest. Liver Physiol.*, 2006, 290 (6):G1105-13), and to modulate the proliferation of lamina propia lymphocytes (Elitsur, Y. and Luk, G. D., *Clin. Exp. Immunol.*, 1991, 85(3):493-7) which are cells associated with the immune system.

The above reports indicate links between caseins and casomorphins (including BCM-7) and gastrointestinal function. These reports are based on studies using milk proteins or caseins generally or on studies using BCM-7 itself. However, to date, there has been no report directly linking the consumption of beta-casein A1 to bowel inflammation. In addition, there have been anecdotal reports from consumers referring to improvements in gastrointestinal function after drinking milk high in beta-casein A2 (and conversely low in beta-casein A1), but these are non-scientific reports and they are non-specific as to the cause of any improvement in function. Furthermore, there are also many anecdotal reports of no improvement effect on consumption of such milk. These reports are conflicting in that they include reports across the digestion effect continuum, from constipation through to diarrhoea. Conclusions cannot be made with confidence from anecdotal reports, particularly in the case of food products and physiological function where the number of variables that can potentially impact on outcomes is very large.

The applicant has now found conclusive scientific evidence for a direct link between the consumption of beta-casein A1 and inflammation of the bowel relative to the consumption of beta-casein A2. Given the myriad of factors in human diet that can influence bowel health, and that milk and milk products contain a wide array of protein components and other components, the applicant's finding of a clear direct association between beta-casein A1 consumption and inflammatory conditions of the bowel is surprising. Notably, the applicant has found evidence, not only of an acute bowel inflammation response to the ingestion of beta-casein A1, but also of long term ongoing inflammation of the bowel resulting from a short term exposure to beta-casein A1.

It is therefore an object of the invention to provide a method for preventing or reducing the risk of inflammation of the bowel, or to at least provide a useful alternative to existing preventative or treatment therapies.

SUMMARY OF THE INVENTION

In a first aspect of the invention there is provided the use of a composition for preventing or reducing the risk of inflammation of the bowel in an animal, wherein the composition contains beta-casein and wherein the beta-casein comprises at least 50% by weight beta-casein A2.

In a second aspect of the invention there is provided a composition for preventing or reducing the risk of inflammation of the bowel in an animal, wherein the composition contains beta-casein and wherein the beta-casein comprises at least 50% by weight beta-casein A2.

In another aspect of the invention there is provided the use of milk in the manufacture of a composition for preventing or reducing the risk of inflammation of the bowel of an animal, wherein the milk contains beta-casein and wherein the beta-casein comprises at least 50% by weight beta-casein A2.

In a further aspect of the invention there is provided a method of preventing or reducing the risk of inflammation of the bowel in an animal comprising the consumption by the animal of a composition containing beta-casein, or providing the composition to the animal for consumption, wherein the beta-casein comprises at least 50% by weight beta-casein A2.

The amount of beta-casein A2 may be any amount in the range of 50% to 100% by weight of the beta-casein, for example at least 90%, at least 99%, or even 100%.

In certain embodiments of the invention, the composition is milk or a milk product. The milk may be milk powder or liquid milk. The liquid milk may be in the form of fresh milk, liquid milk reconstituted from a powder, skim milk, homogenised milk, condensed milk, evaporated milk, pasteurised milk or non-pasteurised milk, UHT milk or any other form of milk. The milk product may be cream, yoghurt, quark, cheese, butter, ice cream, or any other milk product.

The inflammation of the bowel may be, although is not limited to, an inflammatory bowel disease or irritable bowel syndrome. The inflammatory bowel disease may be, although is not limited to, Crohn's disease or ulcerative colitis.

In most embodiments of the invention, the animal is a human. However, in other embodiments, the animal may be a dog, cat, or any other domestic animal where feed is supplemented with milk.

DETAILED DESCRIPTION

Figure 1:
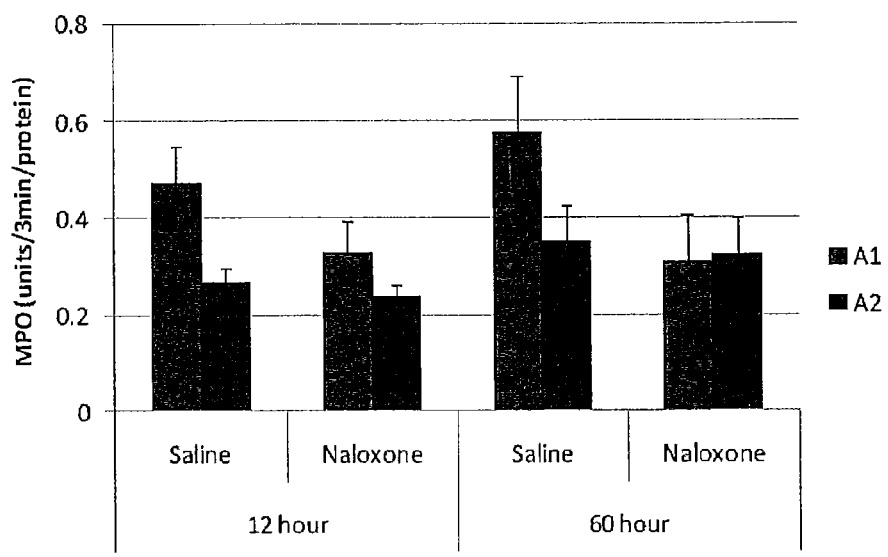
FIG. 1 shows colon myeloperoxidase activity in rats fed the diets of Example 1.

The invention relates to a composition containing the protein beta-casein and its use for preventing inflammation of the bowel or at least reducing the risk of developing inflammation of the bowel. Importantly, the beta-casein is the A2 variant of beta-casein, or makes up at least 50% by weight of the total beta-casein variants present in the composition. The importance of the predominance of the A2 variant in the composition is due to the fact that the applicant has shown that there is a direct link between the A1 variant and biological markers for inflammation of the bowel in humans. Therefore, an improvement in bowel health can be expected if the consumption of the A1 variant is avoided.

The term "inflammation of the bowel" as used in this specification is intended to mean any disease, disorder or condition that is characterised by acute, transitional or chronic and ongoing inflammation of the colon and/or the small intestine. Such diseases, disorders or conditions include, but are not limited to, inflammatory bowel disease (IBD) and irritable bowel syndrome (IBS), in addition to non-specific irritation of the bowel. IBD refers generally to clinically defined and persistent conditions, primarily Crohn's disease and ulcerative colitis.

The term "A1 milk" as used in this specification is intended to mean milk containing beta-casein where that beta-casein is predominantly in the form of beta-casein A1 (or any other beta-casein variant having histidine at position 67 of its 209 amino acid sequence). A1 milk may have a beta-casein component that is greater than 50%, typically greater than 90% (ideally 100%), beta-casein A1.

The term "A2 milk" as used in this specification is intended to mean milk containing beta-casein where that beta-casein is predominantly in the form of beta-casein A2 (or any other beta-casein variant having proline at position 67 of its 209 amino acid sequence). A2 milk may have a beta-casein component that is greater than 50%, typically greater than 90% (ideally 100%), beta-casein A2.

Since the primary, if not only, source of beta-caseins in the diet of most human populations is milk or products derived from milk, and since most milk consumed contains a mixture of the A1 and A2 variants of beta-casein only, the consumption of milk (or products made from such milk) having a high content of the A2 variant will necessarily mean that the consumption of the A1 variant is low. To take this analysis further, if the only dietary source of beta-casein contains the A2 variant and no other variant, the dietary intake of the A1 variant is eliminated and the adverse health consequence of bowel inflammation arising from beta-casein A1 consumption can therefore also be expected to be eliminated.

Accordingly, the invention of this application is based on the reduction or elimination of beta-casein A1 in the diet of animals (especially humans) and this is achieved by ensuring that the beta-casein in beta-casein containing food compositors, especially milk and milk products, is predominantly or even exclusively beta-casein A2.

Ideally, the beta-casein in the composition is 100% beta-casein A2. The complete elimination of beta-casein A1 therefore maximises the associated health benefit by reducing or eliminating altogether the risk of inflammation of the bowel caused by beta-casein A1 (and BCM-7). However, the risk may be reduced in any composition where the beta-casein is predominantly beta-casein A2, that is, any amount between 50% by weight and 100%, including but not limited to 60%, 70%, 75%, 80%, 90%, 95%, 98% and 99% by weight.

Since the invention relates to the use of a composition containing beta-casein where the beta-casein comprises at least 50% by weight beta-casein A2, and as explained above beta-casein A1 and beta-casein A2 are essentially the only beta-casein variants present in milk consumed by most populations, the invention also relates to the use of a composition containing beta-casein where the beta-casein comprises less than 50% by weight beta-casein A1. Preferably, the composition contains less than 60%, 70%, 75%, 80%, 90%, 95%, 98% or 99% by weight beta-casein A1, and ideally no beta-casein A1 at all.

The composition of the invention is typically milk, but may also be any milk-derived product such as cream, yoghurt, quark, cheese, butter, or ice cream. The composition may also be a non-milk product containing beta-casein that has been obtained from milk. The composition may be beta-casein itself, or may be prepared from beta-casein, which beta-casein may be in solid form such as powder or granules or in the form of a solid cake.

While the milk may be obtained from any mammal, including humans, goats, pigs and buffalo, in preferred embodiments of the invention the milk is bovine milk.

The milk may be in the form of fresh milk, milk powder, liquid milk reconstituted from a powder, skim milk, homogenised milk, condensed milk, evaporated milk, pasteurised milk or non-pasteurised milk, UHT milk, or any other form of milk.

The composition of the invention is applicable for consumption by humans primarily, but it should be appreciated that the health benefit is also relevant for some other animals such as cats, dogs and other domestic animals.

Support for the invention is found in the experiments described in the Examples.

In particular, Example 2 relates to the effect of beta-casein A1 and beta-casein A2 diets on myeloperoxidase (MPO) activity in the colon of rats. MPO activity is a marker for inflammation (Krawisz, et al., *Gastroenterology*, 1984, 87(6):1344-1350 and Dommels, Y. E. M., et al., *Genes Nutr.*, 2007, 2(2):209-223). It was found that colon MPO activity increased in beta-casein A1-fed rats compared to beta-casein A2-fed rats indicating an increased level of neutrophil cells in beta-casein A1-fed rats, which is in turn an indicator of inflammatory response. The effect was not observed in rats treated with naloxone (a known opioid receptor antagonist), demonstrating that the effect is mediated through the interaction of BCM-7 with µ-opiate receptors.

Example 3 relates to effects on MPO activity in the jejunum. The results indicate that there was no observable increase in inflammation in the small intestine on consumption of beta-casein A1. This contrasts with Example 2 which showed inflammation in the colon. The result of Example 3 confirms that the inflammation induced by consumption of beta-casein A1 is localised in the colon and not throughout the intestine.

Example 4 relates to concentrations of serum amyloid A (SAA), which is a protein secreted, primarily by the liver, during the acute phase of inflammation (Uhlar, C. M. and Whitehead, A. S., *Eur. J. Biochem.*, 1999, 265(2):501-523). SAA levels are an indicator of systemic inflammation. Example 4 shows that there were no significant differences in plasma SAA concentration between any of the treatment groups. In other words, there was no clear evidence of systemic inflammation from this study.

Example 5, which relates to histology studies, reflects that the inflammation in the colon is subtle and may be subclinical in how it presents. Despite MPO data confirming an inflammatory response of the tissue, this was not visually apparent as evidenced by the lack of significance stemming from wide ranging data sets.

The significance of the SAA and the small intestine MPO experiments is that no evidence in either study of systemic inflammation was observed. This is consistent with a BCM-7 mediated inflammatory response. While not wishing to be bound by any theory, this can be explained because inflammation of the intestine that is mediated by BCM-7 is a localised inflammatory response. In other words, the lack of evidence of systemic inflammation (SAA and histology studies), coupled with evidence of localised inflammation (MPO studies), is a strong indicator that BCM-7 derived from ingestion of foods containing beta-casein A1 causes inflammation of the bowel while not having a systemic effect nor an effect on the small intestine.

The finding is further surprising in light of published evidence that BCM-7 can counter inflammation. For example, it has been reported that BCM-7 reduces oxidative stress in kidneys (Zhang, W., et al., http://www.ncbi.nlm.nih.gov/pubmed/23658831). Oxidative stress is an inflammatory effect. Thus, the reported finding that BCM-7 reduces this inflammatory effect points to the unpredictability of BCM-7 as a factor in health related physiological processes.

Example 6 describes a trial to examine whether beta-casein A1 containing milk has an effect on gastrointestinal symptoms relative to beta-casein A2 containing milk. The key finding is a statistically significant difference in stool consistency following consumption of 100% beta-casein A1 milk and 100% beta-casein A2 milk (p=0.038). The statistical evidence for this is even stronger when women are considered alone (p=0.013). The evidence remains strong when those who considered themselves to be intolerant to milk are excluded from the analyses (p=0.044). It is clear that the beta-casein A1 milk regime relative to the beta-casein A2 milk regime led to overall softer faeces. The compromised water absorption function leading to softer faeces is evidence of a higher level of bowel inflammation when beta-casein A1 is consumed relative to beta-casein A2.

The applicant also investigated and found direct relationships between BCM-7 (from beta-casein A1) and inflammation indicators such as cysteine and glutathione (GSH) levels.

An association between Reactive Oxygen Species (ROS), which are chemically reactive molecules containing oxygen such as oxygen ions and peroxides, and IBD can be inferred from the evidence that increased ROS levels and decreased antioxidant levels are major contributing factors to pathogenic mechanisms in IBD, Crohn's disease and ulcerative colitis. ROS can also potentiate immune reactions in IBD by elevating inflammatory leukocytes. Further, inflammation and inflammatory disease progression are also associated with defects in mucosal antioxidant defences, especially mucosal GSH levels. Drugs with antioxidant properties are reported to show beneficial effects in the treatment of IBD.

Blood levels of cysteine and selenium are critical for the support and maintenance of GSH synthesis, and these in turn are dependent upon the absorption of the food-derived sulfur-containing amino acids cysteine and methionine from the gastrointestinal (GI) tract via the different transporters on the intestinal epithelial border surface.

A deficiency in the essential trace element selenium (Se) is considered a risk factor for several chronic diseases associated with oxidative stress and inflammation in humans, including Crohn's disease. Se is essential for the activity of glutathione peroxide GPX2 or GPX1, both of which are key enzymes involved in regulating the levels of GSH in brain and mucosa. GPX1 is known to be associated with IBD, and its activity depends on the presence of Se.

Among the various amino acid transporters in GI epithelial cells, EAAT3 (excitatory amino acid transporter 3, EAAC1) is selective for cysteine transport and was initially cloned from GI epithelial cells. EAAT3 is most prominently expressed in the small intestine, especially in the terminal ileum, the highest levels being in crypt cells and lower villus regions. This is the major site for multipotent stem cells supporting the epithelial lining of the gut. Hence, there is decreased EAAT3-dependent absorption of cysteine, with the local and systemic consequences of lower GSH levels.

The effects described above are the acute effects of changes mediated by any modulator of EAAT3, especially in the GI tract. However, impaired GI absorption of cysteine, the essential GSH precursor, would not only result in local and systemic oxidative stress, but would also induce the subsequent disruption of normal epigenetic regulation of gene expression. This occurs via methionine synthase enzyme activity and the regulation of S-adenosylmethionine (SAM) levels. SAM acts as a methyl donor for DNA and histone methylation, and converts to S-adenosylhomocysteine (SAH). The methylation capacity of a cell is referred to as SAM/SAH. Adaptive epigenetic responses to changes in redox status are likely to play a critical role in various diseases, especially those that can be traced to interference with antioxidant homeostasis such as inflammation of the GI tract generally, and more specifically IBD and Crohn's disease.

Figure 5:
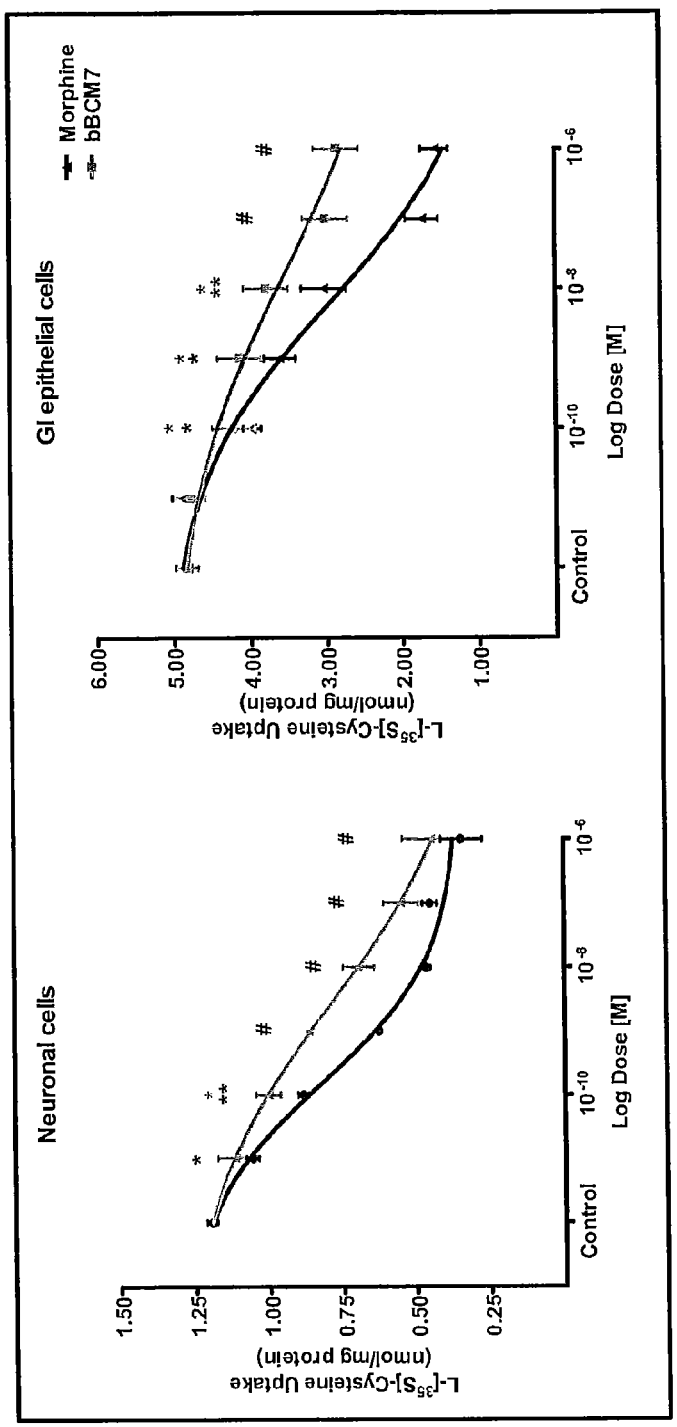
FIG. 5 shows the morphine and BCM-7 concentration dependent uptake of cysteine in neuronal cells and GI epithelial cells.

Example 7 indicates that BCM-7 can inhibit the uptake of cysteine in a concentration-dependent manner with an efficacy order of morphine greater than BCM-7, and IC50 values of 0.16 and 1.31 nM in neuronal cells and 6.38 and 15.95 nM, respectively, in GI epithelial cells (FIG. 5). Inhibition of cysteine uptake was fully developed at 30 minutes and was sustained through 48 hours of morphine or BCM-7 exposure (FIG. 6), indicating a long term chronic effect on the cysteine uptake after single exposure to BCM-7. These effects were μ-opioid receptor mediated as indicated by the blockade in the presence of a selective μ-antagonist and not a delta opioid receptor.

Figure 7:
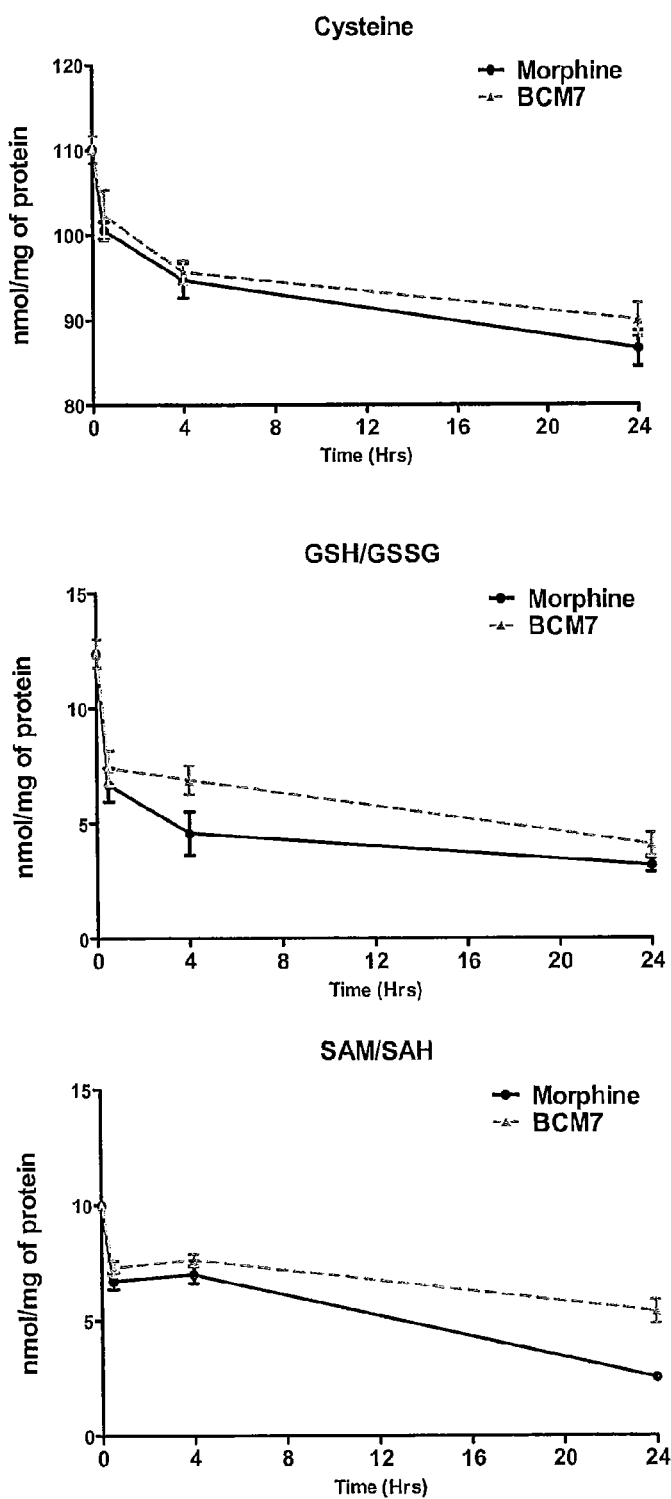
FIG. 7 shows the effect of BCM-7 and morphine on cysteine, GSH/GSSG and SAM/SAH over time.

Example 8 indicates that BCM-7 and morphine caused time-dependent decreases in cysteine and GSH levels. The intracellular levels of cysteine in neuronal cells, the redox status of the cells, reflected by the GSH/GSSG ratio of glutathione (GSH) to its oxidised form glutathione disulphide (GSSG), were also decreased (FIG. 7), potentially indicating an oxidative stress condition. Further, the ratio of SAM/SAH (methylation capacity) was also affected by BCM-7 treatment at different time points (FIG. 7). Hence, BCM-7 induces a reduction in major intracellular antioxidant levels, specifically GSH levels, and has the potential to lead to inflammatory change via the oxidative-stress signalling pathway. Further, the changes mediated in the SAM levels could induce epigenetic changes in genes responsible for inflammatory pathways.

Example 9 illustrates that treatment with the prototypical opioid morphine resulted in 7,592 differentially expressed transcripts (DETs), while BCM-7 treatment yielded 1,467 DETs. 501 DETs were shared by both morphine and BCM-7. Additionally, this result indicates the diseases and disorders that were found to be significantly associated with the observed changes in global DNA methylation. BCM-7 differentially methylated promoter transcripts (DMTs) were associated with inflammatory disease (Table 5). Hence, the acute effects of BCM-7 on GSH antioxidant levels and oxidative stress essentially translate to chronic adaptive gene expression changes. The genes which are altered epigenetically under the influence of BCM-7 are directly involved in regulating cellular function as well as inflammatory disease pathways, and the genes transcriptionally regulated are also involved in cellular functions and redox homeostasis (Table 5).

Figure 8:
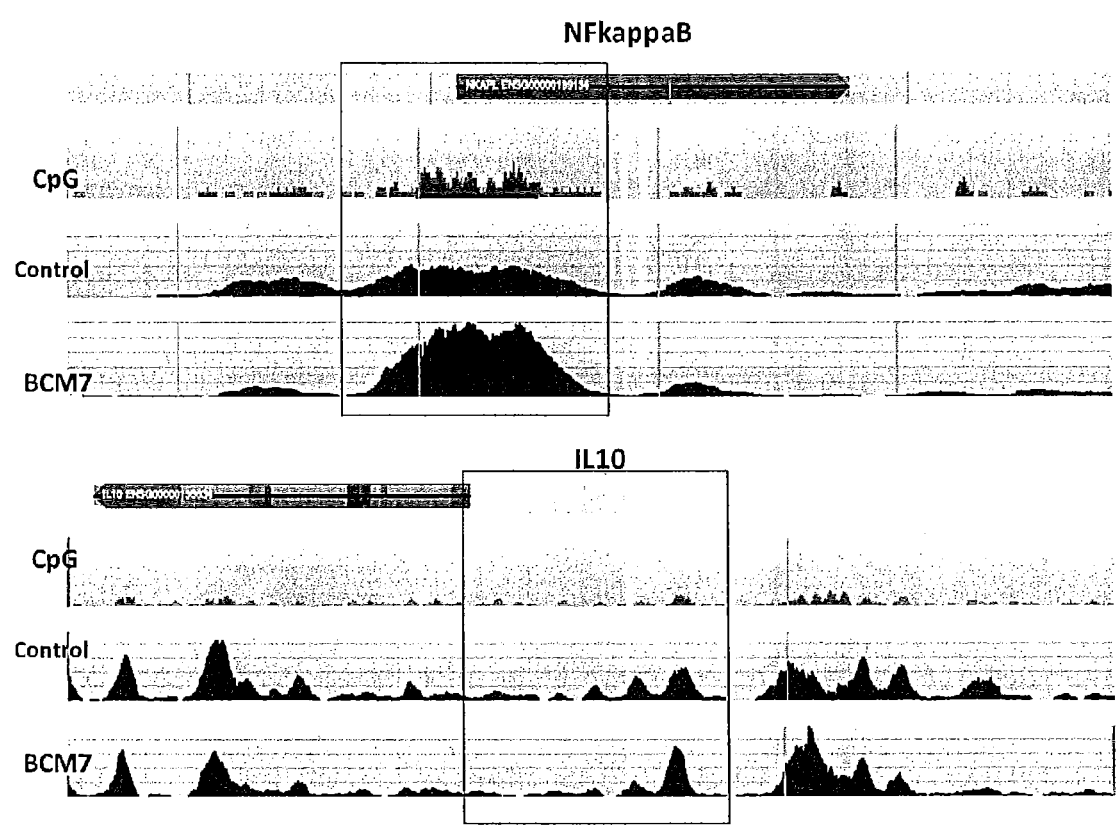
FIG. 8 shows CpG methylation changes in genes implicated in inflammatory response (NFkappaB and IL10) under the influence of BCM-7.
Figure 9:
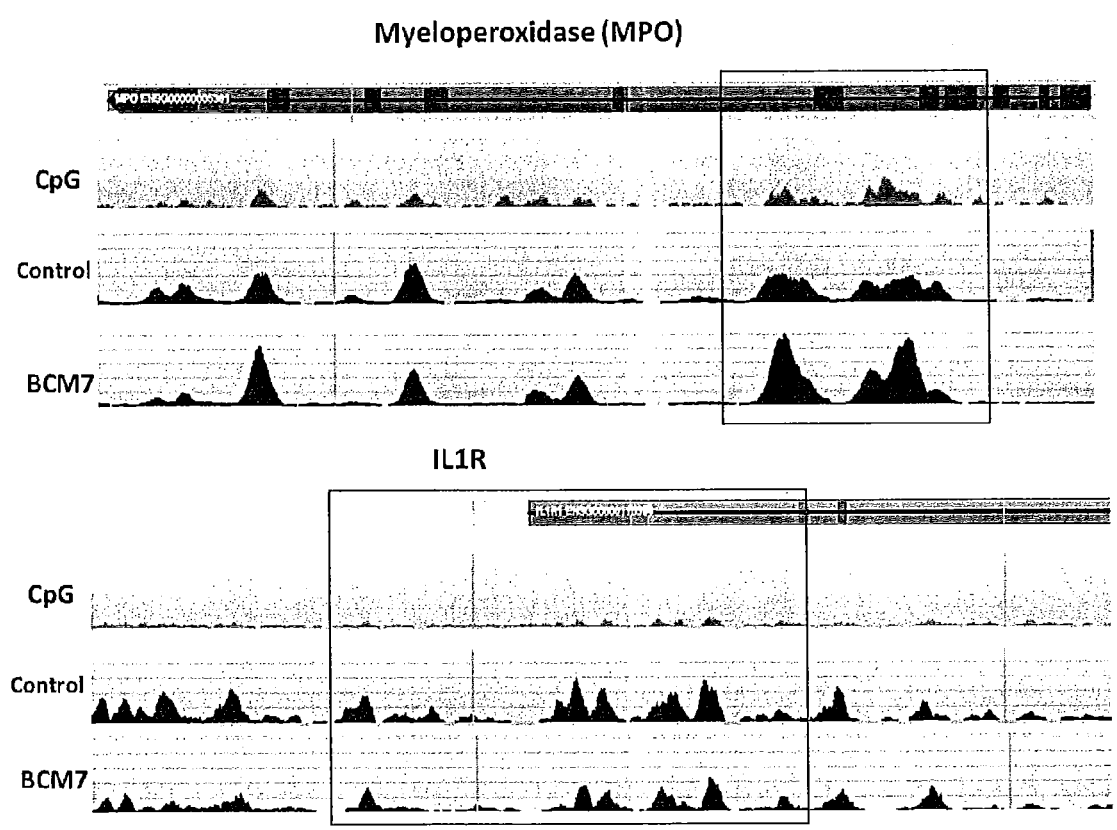
FIG. 9 shows CpG methylation changes in genes implicated in inflammatory response (MPO) and genes implicated in immune response (IL1R).

Example 10 shows the DNA methylation changes in the genes responsible for mediating the inflammatory response under the influence of BCM-7. Cytokines such as NFkappaB and interleukins such as IL1 (FIG. 8) are altered in their epigenetic status after BCM-7 exposure. Hence, the changes in the redox status mediated the long term changes in the epigenetic status of the cytokines. This would serve as a memory of the molecular insults, potentially contributing to long term chronic changes and inflammatory responses in diseases such as IBD. Additionally, the altered epigenetic status is evident from Example 10. Therefore, BCM-7 not only alters MPO activity, as evident from the beta-casein A1 feeding studies, but it also alters the epigenetic status of the MPO gene (FIG. 9).

These studies represent the first clear scientific evidence of a link between beta-casein A1 consumption and inflammation of the bowel. Previously, inconclusive and conflicting anecdotal reports and studies relating to BCM-7 (rather than beta-casein A1 itself) had lead to confusion among those skilled in the art, with many believing there was no such link. Through the applicant's finding, an alternative potential solution to the problems caused by various inflammatory bowel conditions that have been suffered by many people throughout the world for many years, i.e. the avoidance of beta-casein A1 in diet, is now provided. This can be achieved by producing milk having its beta-casein content containing predominantly beta-casein A2 (and absent beta-casein A1) and making such milk, and products derived from that milk, available for the purpose of treating, avoiding or reducing the risk of conditions or symptoms related to inflammation of the bowel. The milk of cows can be tested for the relative proportions of beta-casein A1 and beta-casein A2. Alternatively, cows can be genetically tested for their ability to produce milk containing beta-casein A1 or beta-casein A2 or a combination of both. These techniques are well-known.

The invention has distinct advantages over existing techniques or methods for treating or preventing inflammatory bowel conditions. Most existing techniques or methods rely on medical intervention through pharmaceuticals, stress management or dietary modifications, many of which often have limited or no real success. The present invention provides a solution that is comparatively easy to manage, i.e. converting to a non-beta-casein A1 diet through replacement of "regular" (beta-casein A1 containing) milk in the diet with milk that is known to be high in beta-casein A2, preferably where all beta-casein present is beta-casein A2. The invention is considerably less costly than pharmaceutical intervention, and also avoids any need for wholesale dietary modifications such as the avoidance of dairy products or other common food products.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to.

The invention is further described with reference to the following examples. It will be appreciated that the invention as claimed is not intended to be limited in any way by these examples.

EXAMPLES

Example 1: Feeding Methodology

Seventy two weaned (four week old) male Wistar rats were used. Following a 7-day acclimatisation period on a control diet, the rats were fed for either 12 or 60 hours with one of three diets: 100% A1 diet, 100% A2 diet, control diet (n=6 per treatment). The protein component of the diets were derived from skim milk (for the A1 and A2 diets) and on egg white (for the non-milk protein control diet), and were balanced for energy and macronutrient composition (see Table 1). Fifteen minutes before the end of the time period, rats received either naloxone or saline (control) via intra-peritoneal injection, and were then orally gavaged with a non-digestible tracer, titanium dioxide. Faecal and urine samples were collected at 7 time points over the following 24 hours, and stored at −20° C. (faecal) or −80° C. (urine) until they were analysed.

TABLE 1

Composition of diets

| | Product | | | | | |
| --- | --- | --- | --- | --- | --- | --- |
| | A1 milk diet | | A2 milk diet | | Egg white diet | |
| Ingredient | gm | kcal | gm | kcal | gm | kcal |
| Casein | 0 | 0 | 0 | 0 | 0 | 0 |
| A1 milk powder | 475 | 1691 | 0 | 0 | 0 | 0 |

TABLE 1-continued

Composition of diets

| | Product | | | | | |
| --- | --- | --- | --- | --- | --- | --- |
| | A1 milk diet | | A2 milk diet | | Egg white diet | |
| Ingredient | gm | kcal | gm | kcal | gm | kcal |
| A2 milk powder | 0 | 0 | 468 | 1687 | 0 | 0 |
| DL-methionine | 3 | 12 | 3 | 12 | 0 | 0 |
| Egg whites (dried) | 0 | 0 | 0 | 0 | 200 | 800 |
| Corn starch | 150 | 600 | 150 | 600 | 153 | 612 |
| Sucrose | 288 | 1152 | 294 | 1176 | 500 | 2000 |
| Cellulose, BW200 | 50 | 0 | 50 | 0 | 50 | 0 |
| Corn oil | 45.2 | 406.8 | 43 | 387 | 50 | 450 |
| Mineral mix S10001 | 35 | 0 | 35 | 0 | 35 | 0 |
| Biotin, 1% | 0 | 0 | 0 | 0 | 0.4 | 0 |
| Vitamin mix V10001 | 10 | 40 | 10 | 40 | 10 | 40 |
| Choline bitartrate | 2 | 0 | 2 | 0 | 2 | 0 |
| Total | 1058.2 | 3902 | 1055 | 3902 | 1000.4 | 3902 |

Example 2: Colon MPO Activity

Colon tissue from the rats fed according to Example 1 was quantified for myeloperoxidase (MPO) activity based on an established method (Grisham, M. B., et al., *Methods Enzymol.*, 1990, 186:729-742). Colon tissue (50 mg) was homogenised, partitioned via centrifugation, ruptured by ultrasonic probe and subjected to a freeze-thaw cycle. Endogenous MPO catalyses $H_2O_2$-dependent oxidation of 3,3',5,5'-tetramethyl-benzidine substrate measured colourimetrically at 562 nm. Activity was normalised by a bicinchoninic acid (BCA) (Smith, P. K., et al., *Anal. Biochem.*, 1985, 150(1):76-85) protein determination for the same homogenate. The results are shown in in FIG. 1.

Example 3: Jejunum MPO Activity

Figure 2:
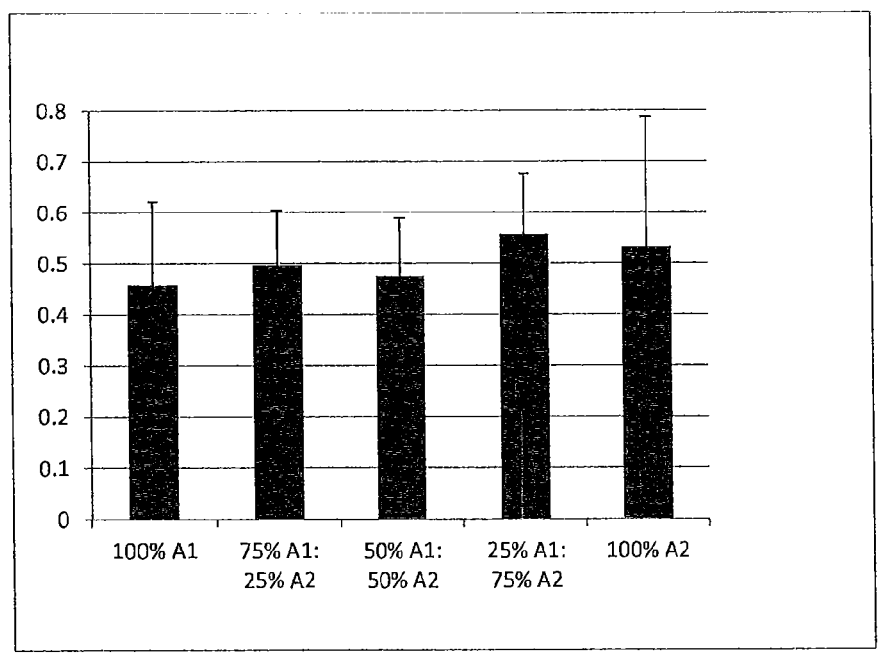
FIG. 2 shows jejunum myeloperoxidase activity in rats fed the diets of Example 1.

In this example, tissue samples taken from the jejunum were analysed. The methodology used was the same as for Example 2. The results are shown in Table 2 and FIG. 2.

TABLE 2

MPO activity in colon and jejunum tissue

| Diet | Jejunum | SD |
| --- | --- | --- |
| 100% A1 | 0.458 | 0.164 |
| 75% A1:25% A2 | 0.497 | 0.107 |
| 50% A1:50% A2 | 0.476 | 0.112 |
| 25% A1:75% A2 | 0.557 | 0.119 |
| 100% A2 | 0.532 | 0.254 |

Example 4: Serum Amyloid A Levels

Figure 3:
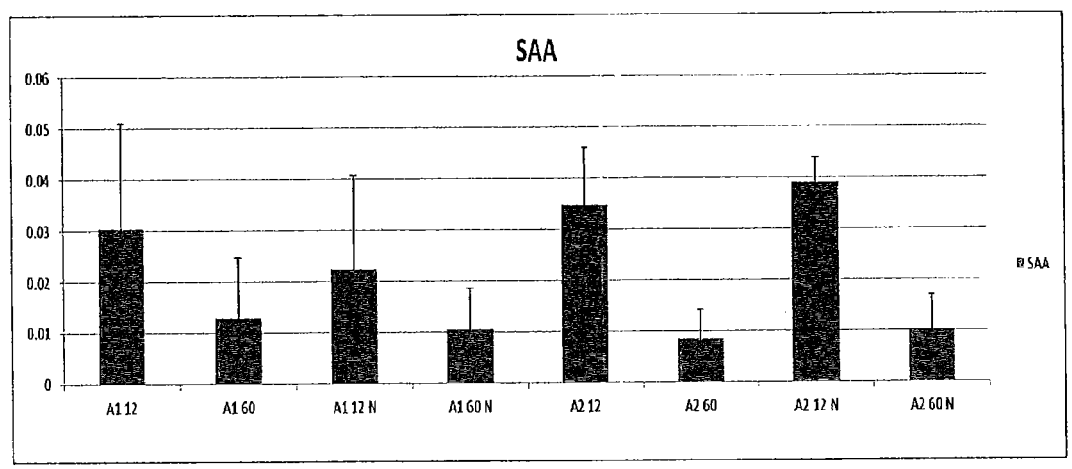
FIG. 3 shows levels of serum amyloid A in plasma in rats fed the diets of Example 1.

SAA levels were measured in plasma taken from the rats fed according to Example 1. Measurements were made using a commercially available ELISA kit (Tridelta Development Limited, Maynooth, Ireland). The results are shown in Table 3 and FIG. 3.

TABLE 3

SAA levels in plasma

|       | SAA    | SD    |
|-------|--------|-------|
| A1 12 | 0.0304 | 0.021 |
| A1 60 | 0.0129 | 0.012 |
| A1 12N| 0.0223 | 0.018 |
| A1 60N| 0.0106 | 0.008 |
| A2 12 | 0.0349 | 0.011 |
| A2 60 | 0.0085 | 0.006 |
| A2 12N| 0.0391 | 0.005 |
| A2 60N| 0.0103 | 0.007 |

Example 5: Intestinal Histology

Figure 4:
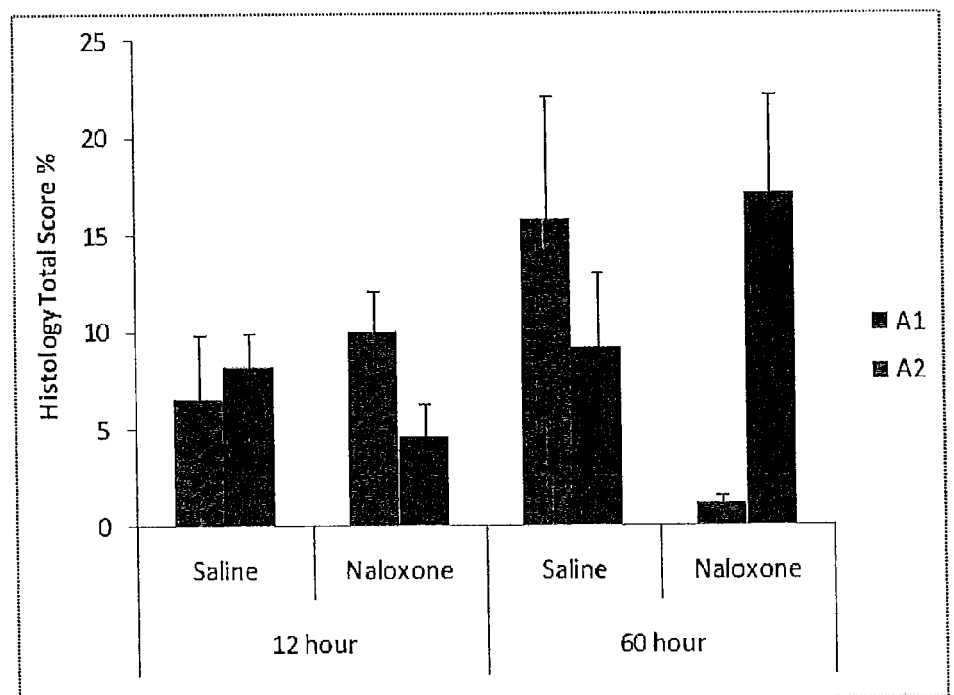
FIG. 4 shows histology scores for intestine sections taken from rats fed the diets of Example 1.

The procedure used for measuring change in morphology in the gastrointestinal tract of rats is based on histological evaluation of haemoxylin and eosin stained tissue sections under a light microscope (Knoch, B. et al., *J. Nutrigenet. Nutrigenomics*, 2009, 2(1):9-28 and Barnett, M. P., *BMC Immunol.*, 2010, 11:39). This method was applied to sections derived from colon tissue of rats fed either the 100% A1 or 100% A2 diets to determine the effects of the beta-casein variants on intestinal inflammation. The results are shown in FIG. 4. The data (mean±SEM) showed that there was a significant ($P<0.05$) difference between the beta-casein A1-fed and the beta-casein A2-fed rats in the 60 hour naloxone group, with the beta-casein A2-fed rats having a significantly higher score. However, the magnitude of these histology scores is not indicative of inflammation, and an overall analysis shows no evidence of an effect of diet, time, or naloxone treatment on histology score.

Example 6: Gastrointestinal Symptoms

In this 8-week randomised, crossover study, participants (n=41) were randomised to one of two groups following a 2-week dairy washout: 1) A1 milk (n=21); or 2) A2 milk (n=20). Participants underwent a second 2-week dairy washout and then crossed over to the alternative intervention milk arm, so that at the end of the 8-week study, all participants (n=37) had completed both milk interventions. Men (12) and 29 women (29), aged 19 to 68 years, were recruited. Exclusion criteria were: (1) milk allergy; 2) medically diagnosed lactose intolerance; 3) pregnancy and lactation; 4) cardiovascular events in the last 6 months; 5) opioid consumption; 6) antibiotic treatment in the previous 8 weeks; and 7) immunosuppressive medication or anti-inflammatory drugs in the 4 weeks prior to screening. Participants began with a 14-day dairy washout period (where dairy milk was replaced with supplied rice milk) before being randomised to 2 weeks on either A1 milk or A2 milk. After completing the first arm of the study, participants completed a second 2 week washout before crossing over to the other milk intervention.

Washout Rice Milk—

Participants were instructed to replace all dairy milk with the supplied rice milk for the 14-day washout periods and to avoid all other dairy foods for the duration of the study. They were provided with information relating to hidden sources of dairy, such as biscuits and chocolate, and were provided with a list of dairy free alternatives. Participants were also supplied with enough rice milk (So Natural Rice Milk, Freedom Foods, Australia) to consume 750 mL rice milk/day, for each of the 14-day washout periods. Rice milk was supplied in 1 litre ultra-high temperature (UHT) packages and had the following nutrition profile per 100 mL: energy 212 kJ, total protein 0.3 g, total fat 1.0 g and carbohydrate 10.4 g.

A1 Milk—

Participants were instructed to replace all dairy milk with the supplied A1 milk and to avoid all other dairy foods and hidden sources of dairy. During the 2-week A1 milk intervention, participants were instructed to consume 750 mL/day (~7.5 g of beta-casein A1) of A1 milk spread out over the day. Nano-LC ESI MS analysis of the A1 milk (APAF, Sydney) found that the A1 proportion of total beta-casein was >99% in the A1 milk.

A2 Milk—

Participants were instructed to replace all dairy milk with the supplied A2 milk and to avoid all other dairy foods and all hidden sources of dairy. During the 2-week A2 milk intervention, participants were instructed to consume 750 mL/day (~7.5 g of beta-casein A2) of the A2 milk spread out over the day. Nano-LC ESI MS analysis of the A2 milk (APAF, Sydney) found that the A1 proportion of total beta-casein was 0.1-0.5%.

Both A1 milk and A2 milk were supplied to participants in 1 litre UHT packages and had the following nutrition profile per 100 mL: energy 189 kJ, total protein 3.1 g, total fat 2.5 g and carbohydrate (including lactose) 5.2 g. Participants recorded the volume of milk consumed per day on compliance calendars. Compliance was calculated as a percentage by dividing the milk volume consumed by the expected milk volume consumption each day and multiplied by 100. A1 milk and A2 milk were provided in identical plain packaging so participants were blinded to the milk intervention they were receiving.

The Bristol Stool Scale (Lewis S. J. and Heaton K. W., *Scand. J. Gastroenterol.* 1997, 32(9):920-4) was used as a surrogate measure of colon transit time. The results are shown in Table 4.

TABLE 4

Bristol stool scale analyses of stool consistency

|  | All participants (n = 36) | | Women only (n = 25) | | Men Only (n = 11) | | Self-described as milk intolerant (n = 8) | | Self-described as milk tolerant (n = 28) | |
|---|---|---|---|---|---|---|---|---|---|---|
| Mean for A1 (±SE) | 3.87 (0.11) | | 3.94 (0.15) | | 3.72 (0.15) | | 4.02 (0.28) | | 3.82 (0.12) | |
| Mean for A2 (±SE) | 3.56 (0.15) | | 3.50 (0.16) | | 3.70 (0.31) | | 3.86 (0.33) | | 3.47 (0.16) | |
| Difference A1 − A2 (±SE) | 0.31 (0.14) | | 0.44 (0.16) | | 0.02 (0.28) | | 0.16 (0.29) | | 0.35 (0.17) | |
| P value for paired t-test | 0.038 | | 0.013 | | 0.156 | | 0.592 | | 0.044 | |
| Median (A1, A2) | 4.0 | 3.8 | 4.0 | 3.8 | 3.7 | 3.8 | .0 | 4.0 | 3.95 | 3.7 |
| 25 percentile A1 | 3.35 | 3.02 | 3.25 | 2.9 | 3.5 | 3.1 | 3.67 | 2.9 | 3.22 | 3.02 |

TABLE 4-continued

Bristol stool scale analyses of stool consistency

| | All participants (n = 36) | | Women only (n = 25) | | Men Only (n = 11) | | Self-described as milk intolerant (n = 8) | | Self-described as milk tolerant (n = 28) | |
|---|---|---|---|---|---|---|---|---|---|---|
| 75 percentile | 4.2 | 4.07 | 4.3 | 4.0 | 4.2 | 4.3 | 4.6 | 4.7 | 4.2 | 4.0 |
| P value for Wilcoxon signed ranks test | 0.085 | | 0.028 | | 0.824 | | 0.598 | | 0.115 | |

Example 7: Effect of BCM-7 on Uptake of Cysteine

Figure 6:
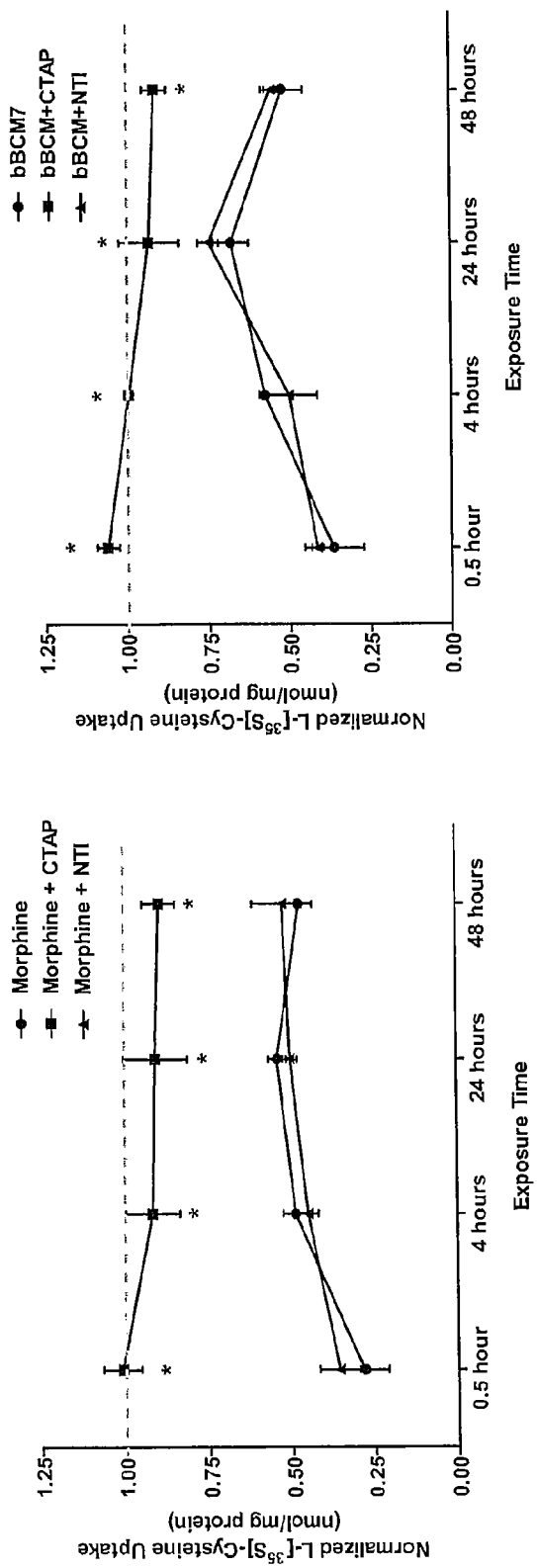
FIG. 6 shows the uptake of cysteine in neuronal cells and GI epithelial cells over time.

Radiolabelled [$^{35}$S]-cysteine uptake assay was performed in Caco-2-GI epithelial cells and neuronal cells, in the presence of BCM-7 released from A1 milk, and compared against untreated controls as well as morphine; a prototypical opioid receptor agonist. Pre-treatment in cells was performed for different time points for 30 min, 4, 24 and 48 h as described previously (Trivedi M., et al.; Mol. Pharm., 2014). Briefly, SH-SY5Y human neuronal cells and Caco-2 Gut epithelial cells were plated in six-well plates and were pretreated with drugs and incubated for various times prior to measuring uptake. Media were aspirated and cells were washed with 600 µL of HBSS at 37° C. Non-radioactive HBSS was aspirated, replaced with 600 µL of 37° C. HBSS containing [$^{35}$S]-cysteine, (1 µCi/1 mL), 10 µM unlabelled cysteine and 100 µM DTT, and the cells were incubated for 5 min. The [$^{35}$S]-cysteine/HBSS mixture was aspirated and treatment was terminated by two washes with ice-cold HBSS. Cells were then lysed with 600 µL of dH$_2$O, scraped, collected in 1.5 mL microcentrifuge tubes, and sonicated for 10 s. 100 µL of each sample was aliquoted for protein assay. 200 µL of each sample (in triplicate) was aliquoted into scintillation vials with 4 mL of scintillation fluid, vortexed, and counted for radioactivity, normalized against protein content. Additionally, the cysteine uptake effects of morphine and BCM-7 were also characterised in the presence of D-Phe-Cys-Tyr-D-Trp-Arg-Thr-Pen-Thr (CTAP), a selective µ-antagonist, and the delta antagonist naltrindole (NTI). The results are shown in FIGS. 5 and 6. Each * symbol in these Figures indicates a statistically significant difference ($p<0.05$) compared against the untreated control, and each #symbol indicates a statistically significant difference ($p<0.005$) compared against the untreated control.

Example 8: Effect of BCM-7 on GSH Levels

This example investigated whether decreases in cysteine uptake as observed in Example 7 could potentially translate into GSH changes and affect antioxidant levels. The intracellular levels of GSH were measured with BCM-7 as well as morphine for different times (30 min, 4 h, and 24 h) with the use of HPLC and an electrochemical gradient detection method used previously (Hodgson et al., J. Alzh. Dis. 2013, Trivedi M., et al., Mol. Pharm. 2014). Briefly, SH-SY5Y neuronal cells were grown to confluence in α-MEM. Media was aspirated and the cells were washed twice with 1 mL of ice cold HBSS. HBSS was aspirated and 0.6 mL ice cold dH$_2$O was added to the cells. The cells were scraped from the flask/dish and suspended in dH$_2$O. The cell suspension was sonicated for 15 s on ice and 100 µL of the suspension was used to determine the protein content. The remaining lysate was added to a microcentrifuge tube and an equal volume of 0.4 N perchloric acid was added, followed by incubation on ice for 5 min. Samples were centrifuged at 5,000×g and the supernatant transferred to new microcentrifuge tubes. 100 µL of sample was added to a conical micro-autosampler vial and kept at 4° C. in the autosampler cooling tray. 10 µL of this sample was injected into the HPLC system.

The separation of redox and methylation pathway metabolites was accomplished using an Agilent Eclipse XDB-C8 analytical column (3×150 mm; 3.5 µm) and an Agilent Eclipse XDB-C8 (4.6×12.5 mm; 5 µm) guard column. Two mobile phases were used: Mobile Phase A was 0% acetonitrile, 25 mM sodium phosphate, 1.4 mM 1-octanesulfonic acid, adjusted to pH 2.65 with phosphoric acid. Mobile Phase B was 50% acetonitrile. The flow rate was initially set at 0.6 mL/min and a step gradient was used: 0-9 min 0% B, 9-19 min 50% B, 19-30 min 50% B. The column was then equilibrated with 5% B for 12 min prior to the next run. Temperature was maintained at 27° C. The electrochemical detector was an ESA CoulArray with BDD Analytical cell Model 5040 and the operating potential was set at 1500 mV. Sample concentrations were determined from the peak areas of metabolites using standard calibration curves and ESA-supplied HPLC software. Sample concentrations were normalised against protein content. In some cases samples were diluted in mobile phase as needed or up to 50 µl of sample was injected to assure that thiol levels were within the range of the standard curve. The results are shown in FIG. 7.

Example 9: Effect of BCM-7 on DNA Methylation and Gene Expression Levels

The changes in SAM/SAH could potentially affect global DNA methylation, influencing the genes involved in various functions. The global DNA methylation levels induced by BCM-7 were investigated using methyl-CpG binding domain (MBD) protein-enriched genome sequencing (MBD-seq) as described previously (Trivedi M., et al., Mol. Pharm. 2014), whereas mRNA translation microarray data was obtained using Agilent V3 microarray chip, from non-treated control SH-SY5Y cells and cells treated for 4 hours with 1 µM BCM-7.

Briefly, genomic DNA was extracted from samples with the Easy DNA kit (Invitrogen K1800-01) using the appropriate protocol for cell lines. Fragmentation was performed on Covaris S2 with the following settings: duty cycle 10%, intensity 5, 200 cycles per burst during 200 sec. Fragments were obtained having an average length of 200 bp. The power mode is frequency sweeping, temperature 6-8° C., water level 12. A maximum of 5 µg was loaded in 130 µl Tris-EDTA in a microtube with AFA intensifier. For samples with less DNA input (down to 500 ng) the DNA was diluted 1:5 in TrisEDTA. DNA with an input from 5-3 3 µg was analysed on the Agilent 2100 using a DNA 1000 chip. DNA with an input lower than 3 µg was concentrated in a rotary evaporator to 25 μl and the fragment distribution was checked on a high sensitivity DNA chip. Methylated DNA was captured using the MethylCap kit (Diagenode, Belgium). The yield was typically between 0.5 and 8 ng of total captured DNA. Fragments were subsequently sequenced using an Illumina Genome Analyzer II. The concentrations of fragmented and captured DNA were determined on a Fluostar Optima plate reader with the Quant-IT PicoGreen dsDNA Assay Kit (Invitrogen P7589) at 480/520 nm.

To prepare the DNA library, a DNA Sample Prep Master Mix Set 1 (NEB E6040) was used in combination with a Multiplexing Sample Preparation Oligo Kit (96 samples, Illumina PE-400-1001). The entire fragmented DNA was utilised and followed the NEB protocols, using the multiplexing sequencing adapters provided in the Multiplexing Sample Preparation Oligo Kit. Size selection of the library was carried out on a 2% agarose gel (Low Range Ultra Agarose Biorad 161-3107). A 1 Kb Plus ladder (Invitrogen 10787-018) was used and a gel was run at 120 V for 2 hrs. A fragment of 300 bps+/−50 bps was excised and eluted on a Qiagen Gel Extraction Kit column (Qiagen 28704) and eluted in 23 μl EB.

The Illumina library amplification index protocol was used with the following alterations: 22 μl DNA was used and performed 21 cycles run. The sample was purified on a Qiaquick PCR Purification column (Qiagen 28101) and eluted in 50 μl EB, 1:5 diluted, concentrated in a rotary evaporator to 10 μl. 1 μl was applied to a Agilent 2100 HS DNA chip and the concentration was determined by smear analysis on the Agilent 2100. The samples were diluted to 10 nM. After denaturation with NaOH the samples were diluted to 16 μM. The Paired-End flow cell was prepared according to the Cluster Station User Guide. Sequencing was performed according to the HiSeq user guide (performing a Multiplexed PE Run), with 2×51 cycles for the paired end runs.

For whole genome microarray hybridisations, 500 ng of total RNA from each sample was labelled with fluorescent dye (Cy3; Amersham Biosciences Corp, Piscataway, NJ) using the Low RNA Input Linear Amplification Labelling kit (Agilent Technologies, Palo Alto, CA) following the manufacturer's protocol. The amount and quality of the fluorescently labelled cRNA was assessed using a NanoDrop ND-1000 spectrophotometer and an Agilent Bioanalyzer. According to manufacturer's specifications, 1.6 mg of Cy3-labeled cRNA was hybridized to the Agilent Human Whole Genome Oligo Microarray (Agilent Technologies, Inc., Palo Alto, CA) for 17 hrs prior to washing and scanning. Data was extracted from scanned images using Feature Extraction Software (Agilent Technologies, Inc., Palo Alto, CA).

Whole genome DNA MBD-seq revealed differentially methylated promoter transcripts (DMTs), as defined by false discovery rate (FDR)<0.1 and mRNA microarray data, revealed differentially expressed transcripts (DETs), defined by FDR<0.1. Transcripts included both genes and non-coding RNAs that were differentially methylated/transcribed. The epigenetic changes as well as the transcription changes induced by BCM-7 in specific biological or functionally relevant pathways were evaluated using the Ingenuity Pathway Analysis (IPA) tool and pathways exhibiting the highest impact were identified. The results are shown in Table 5.

TABLE 5

Inflammatory Diseases and BCM-7 Differentially Expressed Transcripts

| Disease or Disorder | P-Value for DMTs |
|---|---|
| Inflammatory Disease | $3.96 \times 10^{-3}$ to $4.51 \times 10^{-2}$ |
| Disease or Disorder | P-Value for DETs |
| Cellular homeostasis | $1.27 \times 10^{-4}$ to $3.28 \times 10^{-2}$ |
| Post Translational Modifications | $2.41 \times 10^{-6}$ to $1.84 \times 10^{-2}$ |

Example 1D: Effect of BCM-7 on Epigenetic Status of Cytokines

Several individual cytokines are reported to be involved in mediating the inflammatory response in diseases such as IBD and Crohn's disease. NFKappaB is one example. Similarly, interleukins such as IL1, IL10 IL33 etc., are also reported to be involved in mediating the inflammatory response in IBD. The epigenetic effects of BCM-7 on interleukins and NFKappaB were investigated using the method described above in Example 9. FIGS. 8 and 9 show the effect of BCM-7 on the DNA methylation changes intragenic or near the promoter region of these genes, namely MPO, IL1R, IL10 and NFKappaB-activating protein. "CpG" denotes the normal level of CpG islands (high frequency of cytosine-guanine sites) noted in that specific gene locus. "Control" indicates non-treated controls.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method of treating irritable bowel syndrome in an adult human in need thereof and having a diet comprising bovine milk or a bovine milk product comprising beta-casein A1 and beta-casein A2, wherein the method comprises the human replacing the bovine milk or bovine milk product in their diet with bovine milk or bovine milk product containing no beta-casein A1, and wherein the irritable bowel syndrome is induced by beta-casomorphin-7 (BCM-7) only.

2. The method of claim 1, wherein the milk is fresh milk, milk powder, liquid milk reconstituted from powder, skim milk, homogenised milk, condensed milk, evaporated milk, pasteurised milk, non-pasteurised milk, or UHT milk.

3. The method of claim 1, wherein the milk product is cream, yoghurt, quark, cheese, butter, or ice cream.

4. The method of claim 1, wherein the adult human is a woman.

\* \* \* \* \*